United States Patent
Frey et al.

[19]

[11] Patent Number: 6,033,392
[45] Date of Patent: *Mar. 7, 2000

[54] IV POLE BAG FABRICATED FROM ANTI-MICROBIAL MATERIAL

[76] Inventors: John W. Frey, 18534 Mold Board Ct., Justin, Tex. 76247; George A. Hird, 466 Lake Washington Dr., West Glocester, R.I. 02816

[ * ] Notice: This patent issued on a continued prosecution application filed under 37 CFR 1.53(d), and is subject to the twenty year patent term provisions of 35 U.S.C. 154(a)(2).

[21] Appl. No.: 08/662,437

[22] Filed: Jun. 10, 1996

[51] Int. Cl.⁷ .......................... A61B 19/00; B65D 83/10; B65D 33/16
[52] U.S. Cl. .......................... 604/403; 206/365; 283/22; 283/84; 283/116
[58] Field of Search .................. 383/9, 22, 84, 383/86, 211, 116, 113, 109; 206/365, 366, 370, 438, 210; 604/408–410, 403; 128/849

[56] References Cited

U.S. PATENT DOCUMENTS

| | | | |
|---|---|---|---|
| 3,070,280 | 12/1962 | Richmond | 206/632 |
| 3,112,747 | 12/1963 | Cowley | 206/365 |
| 3,494,726 | 2/1970 | Barasch | 206/365 |
| 3,616,991 | 11/1971 | Beck | 383/22 |
| 3,937,219 | 2/1976 | Karakashian | 206/365 |
| 4,189,053 | 2/1980 | Stagnitto et al. | 383/22 |
| 4,372,313 | 2/1983 | Villari et al. | 604/317 |
| 5,176,665 | 1/1993 | Watanbabe et al. | 604/317 |
| 5,240,484 | 8/1993 | Genovese et al. | 55/279 |
| 5,540,500 | 7/1996 | Tanaka | 383/43 |

FOREIGN PATENT DOCUMENTS 2007944   1/1970   France .

*Primary Examiner*—Ronald Stright
*Assistant Examiner*—David J. Cho

[57] ABSTRACT

A bag for securing an irrigation syringe to an IV pole includes a first sheet of flexible material having four sides, and a second sheet of flexible material having four sides which are sealingly attached to the first sheet along three sides thereof. The unsealed side of the second sheet defines a mouth for accessing the interior of the bag. The interior region is sized for receiving the irrigation syringe therein. A flap which is sealingly attached to the first sheet at the top of the sheet extends over the mouth in such a manner that it closes the mouth of the bag to prevent airborne particulates from entering the bag, thus protecting the syringe. A slot formed in the first sheet is provided for securing the bag to an IV pole. The inner surfaces of the first and second sheets and the flap are treated with anti-microbial material for substantially inhibiting bacteria on the syringe.

4 Claims, 3 Drawing Sheets

IV POLE BAG FABRICATED FROM ANTI-MICROBIAL MATERIAL

BACKGROUND AND SUMMARY OF THE INVENTION

This invention relates generally to flexible plastic bags, and more particularly to a plastic bag which is constructed and arranged for receiving an irrigation syringe therein and for securing the syringe to an IV pole or other hanger, the bag being treated with anti-microbial material which is effective in inhibiting bacteria on both the interior and exterior of the bag.

Prior art irrigation syringe packaging which is adapted to hold a sterilized syringe, in one known embodiment, includes a plastic pouch which is wrapped (as by heat sealing) about the syringe. In such a packaging arrangement, the plastic pouch is typically torn open and discarded after the syringe is removed. This construction has the advantages of being reliable in use since it maintains the syringe in a sterile condition, and is relatively inexpensive to implement. However, after the syringe is removed, the destroyed packaging cannot be effectively reused for storing the syringe in a dust-free, uncontaminated environment. Thus, any bacteria on the syringe remains thereon if stored in an unprotected area or if not properly treated before entering the bag.

In another known syringe holder, the holder comprises a cylindrical plastic tube which is shaped to receive the assembled syringe therein, and a cap for maintaining the syringe in the tube. The tube and cap arrangement are sterilized in the well-known manner. Although this construction solves the problem of being able to reuse the holder for storing the syringe in a dust-free environment after it has been used, its cylindrical shape makes it difficult for the user of the syringe to store the syringe effectively without risk that the holder will fall off a table on which it is placed, for example, and onto the floor. Moreover, any bacteria on the syringe remains thereon since the holder lacks any means for inhibiting the bacteria.

Accordingly, among the several objects of the present invention are the provision of an improved bag which is adapted to receive an irrigation syringe therein, the bag being capable of inhibiting any bacteria or the like (e.g., fungi) present on the syringe; the provision of such a bag which is capable of being supported by an IV pole after it is used or partially used for safely storing the syringe for future use; the provision of such a bag which is especially suited for maintaining the syringe in a dust-free environment; the provision of such a bag which is simple in construction and cost-efficient to manufacture; and the provision of such a bag which is easy to use.

In general, the present invention is directed to a bag for securing an irrigation syringe to an IV pole comprising a first sheet of flexible material having four sides, and a second sheet of flexible material having four sides which are sealingly attached to the first sheet along three sides thereof. The unsealed side of the second sheet defines a mouth for accessing the interior of the bag. The interior region is sized for receiving the irrigation syringe therein. A flap which is sealingly attached to the first sheet at the top of the sheet extends over the mouth in such a manner that it closes the mouth to protect the syringe placed in the interior region of the bag from airborne particulates entering the bag. Suitable means is provided for securing the bag to an IV pole. The entire bag (first and second sheets and the flap) is manufactured with an anti-microbial material (incorporated into the extrusion process) for inhibiting bacteria on both the interior and exterior of the bag.

In a preferred embodiment, the second sheet has an upper surface with a strip of adhesive applied thereto for securing and maintaining the flap against the second sheet when the flap is positioned to extend over the mouth in a closed position. The flap is adapted to be peeled away from the second sheet and folded back over to an open position for exposing the mouth thereby enabling access of the syringe from the interior region of the bag. Also, the IV pole securing means comprises a slot formed along the seal of the flap and the first sheet. The slot is adapted to receive a hanger portion of the IV pole therethrough for hanging the bag on the IV pole. Moreover, the bag is manufactured with a patient information form or legend on the outer surface of the second sheet. The information for is adapted to be written on wherein the patient's name, room number, date and any other specific instructions can be provided.

Other objects, features and advantages of the invention shall become apparent as the description thereof proceeds when considered in connection with the accompanying illustrative drawings.

BRIEF DESCRIPTION OF THE DRAWINGS

In the drawings which illustrate the best mode presently contemplated for carrying out the present invention.

Corresponding reference numerals designate corresponding parts throughout the several views of the drawings.

DETAILED DESCRIPTION OF THE PREFERRED EMBODIMENT

Figure 3:
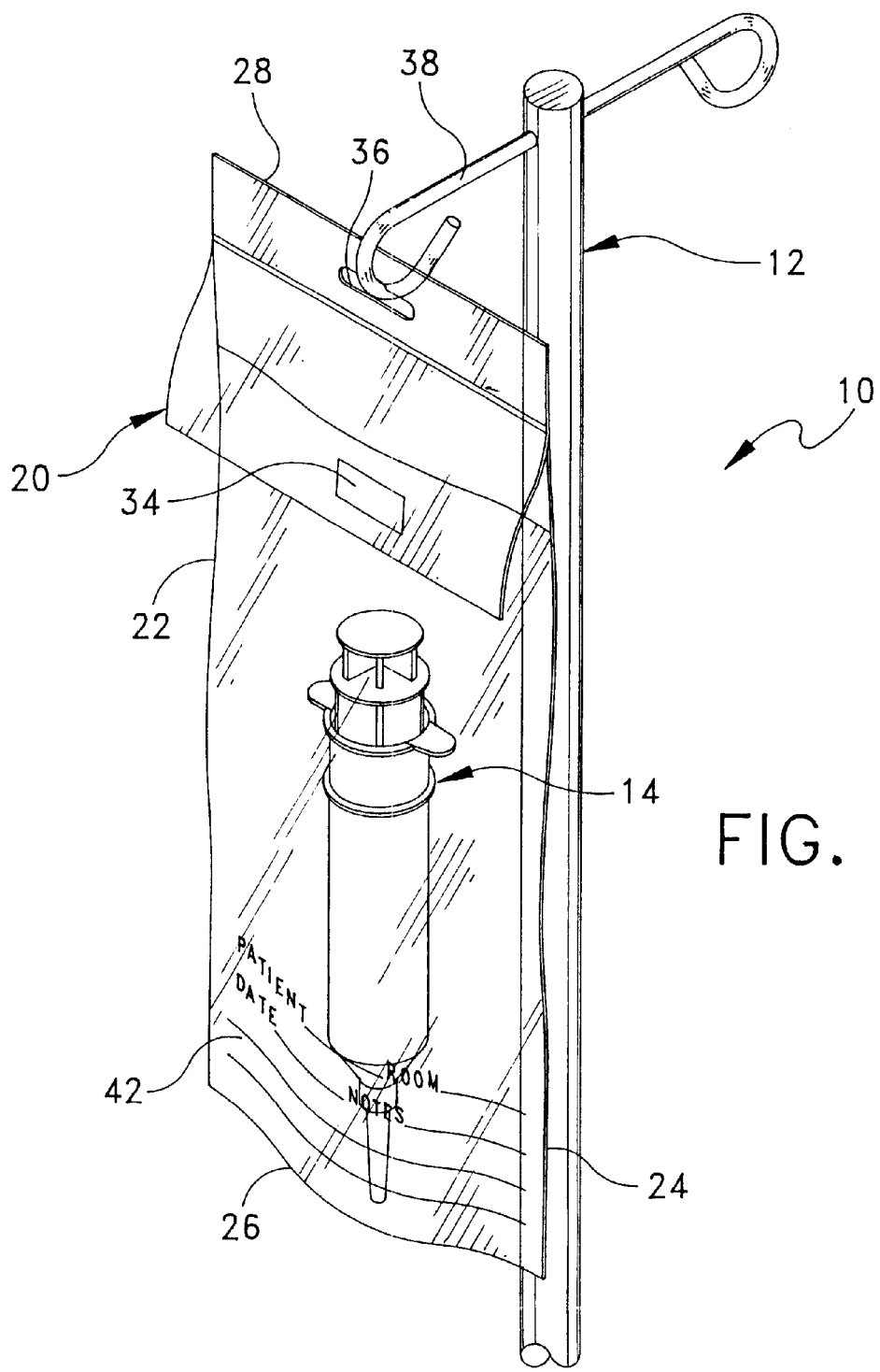
FIG. 3 is a perspective view similar to FIG. 1 illustrating the bag being supported by an IV pole.

Referring now to the drawings, there is generally indicated at 10 a rectangularly-shaped, flexible bag of the present invention which is capable of being hung on and supported by an IV pole, generally indicated at 12 in FIG. 3. Preferably, the bag 10 is fabricated from transparent flexible plastic material (e.g., vinyl) which is treated with anti-microbial material. The bag 10 is of sufficient strength and rigidity for containing a syringe therein, the syringe being generally indicated at 14 throughout the drawings. The syringe 14 is of standard construction and well-known in the art of irrigation systems.

Figure 2:
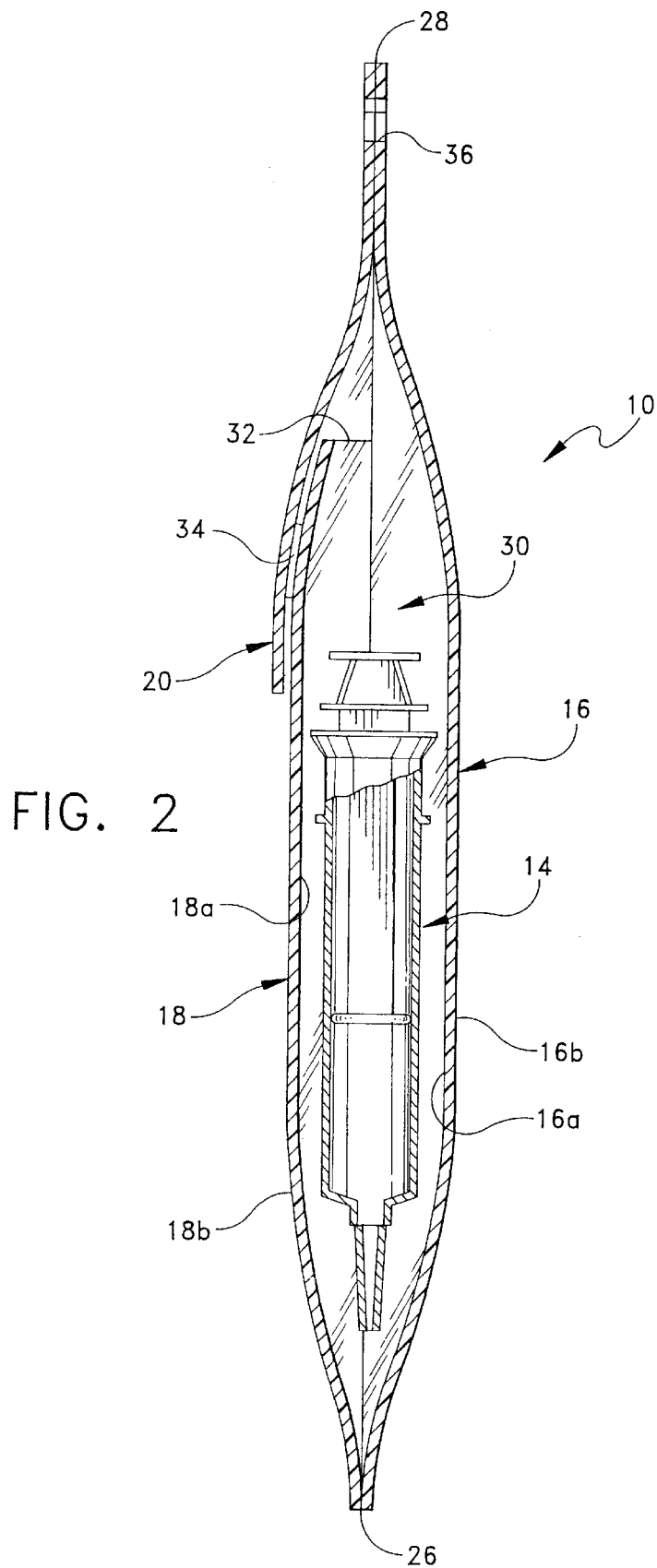
FIG. 2 is an elevational, cross section view taken along line 2—2 of FIG. 1.

As shown best in FIG. 2, the bag 10 comprises a first sheet generally indicated at 16, and a second sheet generally indicated at 18, the first sheet 16 being longer than the second sheet 18 so that it extends above the second sheet 18 when the sheets are placed adjacent one another. A top flap of sheet material is generally indicated at 20, the purpose of which will be described in greater detail below.

Figure 1:
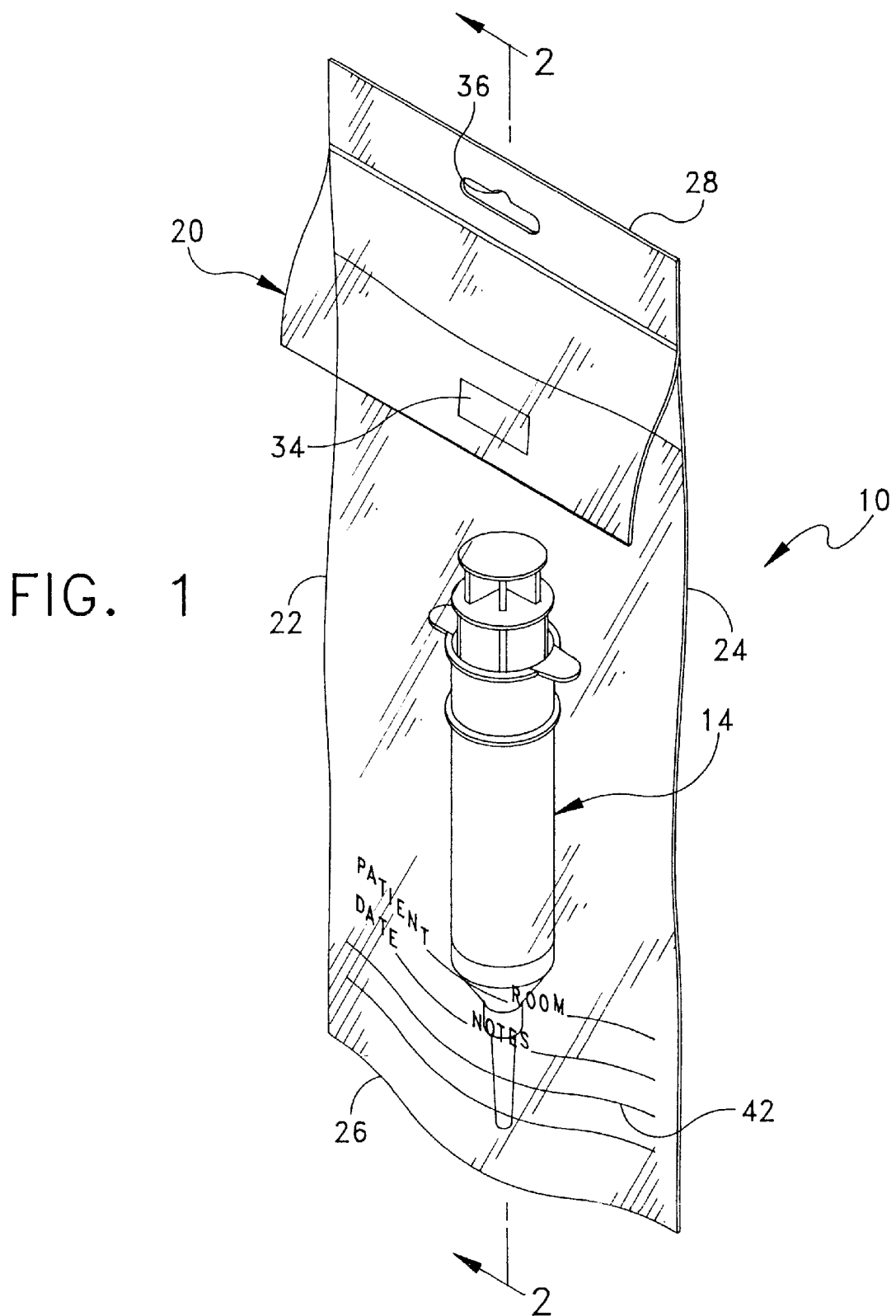
FIG. 1 is a perspective view of a bag of the present invention being shown with an irrigation syringe stored therein.

Referring to FIGS. 1 and 2, the bag 10 has four sides represented by reference numerals 22, 24, 26 and 28. The first and second sheets 16, 18 are sealed together in the conventional fashion to form an interior region generally indicated at 30 (see FIG. 2) which is accessible through a mouth 32. More specifically, the second sheet 18 has three sides corresponding to sides 22, 24 and 26 of the bag 10 which are sealed (as by heat sealing) to the first sheet 16 along three of its sides (also corresponding to sides 22, 24 and 26 of the bag 10). This arrangement defines the interior region 30 wherein the mouth 32 is formed by the unsealed side 28 of the bag 10. The interior region 30 of the bag 10 is sized for receiving therein the irrigation syringe 14. The syringe 14 may be placed within the interior region 30 of the bag 10 by sliding it through the mouth 32 in a position where it is contained within the bag 10.

The bag 10 of the present invention, as mentioned briefly above, has its inner surfaces coated or treated with anti-microbial material for inhibiting bacteria on the syringe 14. More particularly, the inner surfaces 16a, 18a of the first and second sheets 16, 18, respectively are treated with an anti-microbial material which is incorporated into the extrusion process of the bag manufacturing (see FIG. 2). It should be noted that the outer surfaces 16b, 18b are also treated due to the incorporation of the anti-microbial agent into the extrusion process. Moreover, the flap 20 is also treated due to the incorporation of the anti-microbial agent into the extrusion process. Thus, when the syringe 14 is inserted in the interior region 30 of the bag 10, the syringe is completely surrounded by the anti-microbial material which inhibits bacteria on the syringe 14 thereby improving the sterility and overall effectiveness of the syringe.

Still referring to FIGS. 1 and 2, the mouth 32 of the bag 10 is closed by the flap 20 which is sealingly attached to the first sheet 16 at the top of the sheet in a well-known manner. The flap 20 extends over the mouth 32 so that it closes the mouth 32 for preventing the syringe 14 placed in the interior region 30 of the bag 10 from falling out. The outer surface 18b of the second sheet 18 has a strip of adhesive 34 applied thereto for releaseably securing and maintaining the flap 20 against the second sheet 18 in a closed position. Alternatively, the strip of adhesive can be placed on the surface of the flap 20 facing the second sheet 18. To access the interior region 30 of the bag 10, the flap 20 can be peeled away from the second sheet 18 (thereby disengaging the adhesive strip 34 from the flap 20) and folded over to an open position for exposing the mouth 32 thereby enabling the user of the bag 10 to access the syringe 14. The adhesive used to create the adhesive strip 34 is of the pressure sensitive type capable of being repeatedly adhered to and removed from the item on which it is adhered.

Although the closed flap 20 keeps the syringe therein substantially dust-free and contaminant-free, it does not effect an airtight closure. This is important since it is desirable that the closed bag be air-ventilated to minimize undesirable moisture from accumulating with the bag.

Formed along the seal of the first sheet 16 and the flap 20 is an elongate slot which is indicated at 36. As illustrated in FIG. 3, this slot 36 is capable of receiving a looped hanger portion 38 of the IV pole 12 therethrough for hanging the bag 10 on the IV pole 12. The bag 10 is of sufficient strength due to its two-ply construction along the slot 36 for enabling it to be hung on the IV pole 12 without tearing or failing.

Additionally, the second sheet 18 is manufactured with a patient information area or legend 42 which is printed on the outer surface of the second sheet 18. This area 42 is capable of being written on whereby the patient's name, room number, date and any specific instructions can be provided. As shown, blank spaces on the area 42 are provided for receiving this information. The arrangement is such that the information on the information area 42 can be seen by the care-giver when the bag 10 is hung on the IV pole 12.

The method of use of the bag 10 of the present invention is illustrated in FIGS. 1 and 3. The syringe 14 comes pre-packaged in the bag 10 as illustrated in FIG. 1. By opening the flap 20, the syringe 14 can be removed from the bag 10 whereby it is available for use. Information, such as the patient's name and room number, for example, can be written on the information area 42 printed on the outer surface of the second sheet 18 of the bag 10. The bag 10 can then be hung on the looped hanger portion 38 of the IV pole 12 in the manner illustrated in FIG. 3.

After use, the syringe 14 is cleaned (e.g., rinsed thoroughly with hot water) and then placed in the bag 10 wherein the flap 20 is moved adjacent the second sheet 18 and adhered thereto by the adhesive strip 34. In this position, the syringe 14 is safely stored in a substantially dust-free and contaminant-free environment wherein dust and other contaminants are prevented from entering the interior region 30 of the bag 10 due to the flap overlying the mouth 32 of the bag 10. The care-giver can access and reuse the syringe 14 by peeling the flap 20 away from the second sheet 18 and removing the syringe 14 from the interior region 30 of the bag 10.

It should be noted that the bag 10 of the present invention is especially suited for storing the syringe 14 therein and supporting it on the IV pole 12 between uses for the patient it has been utilized. The care-giver is assured that the syringe 14 will be in a condition acceptable for future use since it is securely attached to the IV pole 12 and properly labeled, and that the used syringe is as sterile as possible by virtue of its anti-microbial material applied on the inner surfaces 16a, 18a of sheets 16, 18, respectively. Moreover, the anti-microbial material present on the inner surfaces 16a, 18a of the bag 10 kills-off most of the bacteria remaining on the syringe 14. It should be further noted that the bag 10 of the present invention demonstrated good to excellent antibacterial activity against certain test organisms, along with excellent antifungal properties.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A container for receiving and retaining a syringe, the container comprising:

at least one flexible sheet constructed and arranged to provide an interior region having an opening, said interior region being for receiving and retaining the syringe;

a flap attached along an upper edge of said container, said flap being constructed and arranged to cover said opening to prevent dust and airborne contaminants from entering the container, while allowing air to enter the container for ventilating the container and the syringe;

said at least one flexible sheet and said flap being constructed from a material including an anti-microbial component which inhibits bacteria on the syringe and the container.

2. The container of claim 1, said container comprising first and second flexible sheets attached together at least one peripheral edge of each sheet to form said interior region therebetween.

3. The container of claim 1, wherein said container is reusable and said anti-microbial component inhibits said bacteria through several uses of said container.

4. In combination, a container and a syringe, the container for receiving and retaining the syringe, the container comprising:

at least one flexible sheet constructed and arranged to provide an interior region having an opening, said interior region being for receiving and retaining said syringe;

a flap attached along an upper edge of said container, said flap being constructed and arranged to cover said opening to prevent dust and airborne contaminants from entering the container, while allowing air to enter the container for ventilating the container and said syringe;

said at least one flexible sheet and said flap being constructed from a material including an anti-microbial component which inhibits bacteria on said syringe and said the container.

* * * * *